(12) United States Patent
Tziazas et al.

(10) Patent No.: US 9,646,373 B2
(45) Date of Patent: May 9, 2017

(54) SYSTEM AND METHOD FOR COUNTERFEIT IC DETECTION

(71) Applicant: IEC Electronics Corp., Newark, NY (US)

(72) Inventors: Achilleas Tziazas, Rochester, NY (US); Mark Northrup, Rochester, NY (US); Daniel F. Martinelli, Fairport, NY (US)

(73) Assignee: IEC Electronics Corp., Newark, NY (US)

( * ) Notice: Subject to any disclaimer, the term of this patent is extended or adjusted under 35 U.S.C. 154(b) by 70 days.

(21) Appl. No.: 14/488,553

(22) Filed: Sep. 17, 2014

(65) Prior Publication Data

US 2015/0078518 A1 Mar. 19, 2015

Related U.S. Application Data

(60) Provisional application No. 61/878,865, filed on Sep. 17, 2013.

(51) Int. Cl.
*G01N 23/04* (2006.01)
*G06T 7/00* (2017.01)
*G01N 21/84* (2006.01)
*G06K 9/62* (2006.01)
*G01N 23/203* (2006.01)
(Continued)

(52) U.S. Cl.
CPC ............. *G06T 7/001* (2013.01); *G01N 21/84* (2013.01); *G06K 9/6202* (2013.01); *G01N 23/046* (2013.01); *G01N 23/203* (2013.01); *G01N 23/223* (2013.01); *G01N 2021/95638* (2013.01); *G06T 2207/10116* (2013.01); *G06T 2207/30148* (2013.01)

(58) Field of Classification Search
CPC ........ G01N 23/00; G01N 23/02; G01N 23/04; G01N 23/06; G01N 23/08; G01N 23/083; G01N 23/18; G01N 23/046; A61B 6/5247
USPC .............................................. 378/53, 58, 63
See application file for complete search history.

(56) References Cited

U.S. PATENT DOCUMENTS 8,255,839 B2 * 8/2012 Ivaldi .................. G03F 7/70541
716/50
8,344,485 B1 * 1/2013 Lee ...................... H01L 23/295
257/659
(Continued)

*Primary Examiner* — Jurie Yun
(74) *Attorney, Agent, or Firm* — Brian B. Shaw, Esq.; Harter Secrest & Emery LLP

(57) ABSTRACT

A method for counterfeit IC detection includes: providing a computer, an optical and an X-ray imager; optically imaging a package of one or more ICs; pattern matching the package image to identify an IC type; selecting one or more reference images from a reference library; X-ray imaging one or more ICs; performing in any order: comparing an internal lead frame structure of the one or more ICs to images from the reference library to determine a first numerical indicator; and determining a composition of the lead frame of the one or more ICs and to a corresponding composition from the reference library to determine a second numerical indicator; calculating an indication of authenticity based on the first numerical indicator and the second numerical indicator; and accepting or rejecting the one or more ICs based on the indication of authenticity. A system for counterfeit IC detection is also described.

21 Claims, 8 Drawing Sheets

(51) Int. Cl.
    *G01N 23/223*     (2006.01)
    *G01N 21/956*     (2006.01)

(56) References Cited

U.S. PATENT DOCUMENTS

| | | | |
|---|---|---|---|
| 9,208,394 B2* | 12/2015 | Di Venuto Dayer | G06K 9/00577 |
| 2004/0022355 A1* | 2/2004 | Kaiser | G06K 7/10 378/49 |
| 2014/0258156 A1* | 9/2014 | Tziazas | G06Q 30/0185 705/318 |

* cited by examiner

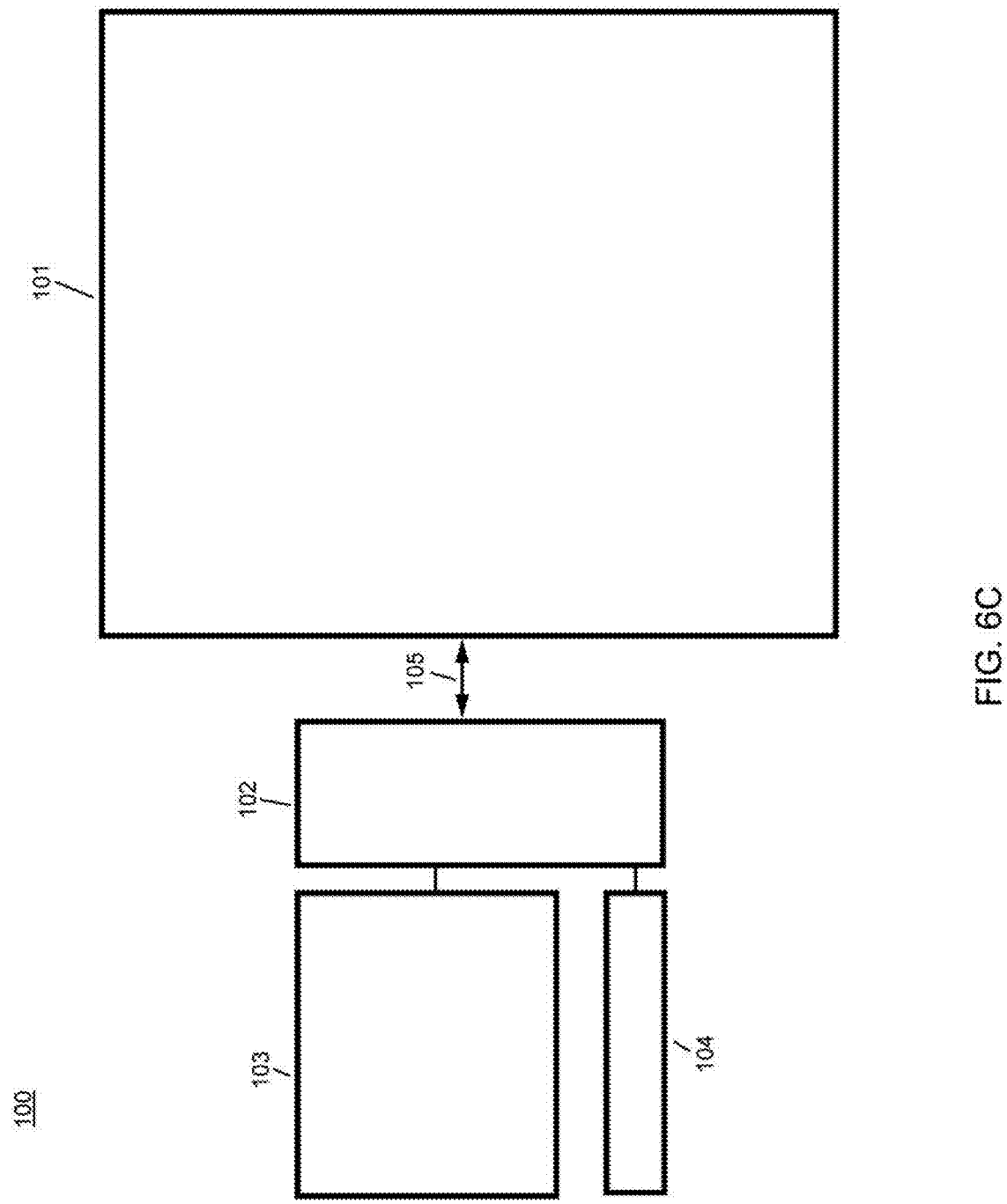

SYSTEM AND METHOD FOR COUNTERFEIT IC DETECTION

CROSS-REFERENCE TO RELATED APPLICATIONS

This application claims priority to and the benefit of co-pending U.S. provisional patent application Ser. No. 61/878,865, SYSTEM AND METHOD FOR COUNTERFEIT IC DETECTION, filed Sep. 17, 2013, which application is incorporated herein by reference in its entirety.

FIELD OF THE APPLICATION

The invention relates to counterfeit IC detection and more particularly to non-destructive IC authentication.

BACKGROUND

Counterfeit integrated circuits (ICs) cost the electronics industry millions of dollars in economic injury. Beyond direct loss related to replacing counterfeit parts or circuit boards with installed counterfeit parts, there can be secondary injury to users of equipment that can malfunction from underperforming or non-performing counterfeit ICs. Such secondary injuries can range from reduced productivity to loss of life where, for example, the malfunctioning or underperforming counterfeit IC is installed in a safety of life system, medical apparatus, or military aircraft.

With growing IC industry awareness of the counterfeit IC problem, the IC industry continues to add new counterfeit detection schemes to IC production lines. Unfortunately, such newly implemented techniques do little to facilitate counterfeit detection of obsolete IC types, many of these ICs having been originally manufactured decades ago.

SUMMARY

According to one aspect, A method for counterfeit IC detection includes: providing a computer, an optical imager communicatively coupled to the computer, an X-ray imager communicatively coupled to the computer, the computer programmed to perform the counterfeit IC detection; imaging optically a package of one or more ICs to provide a package image of the one or more ICs; pattern matching the package image of the one or more ICs to identify by computer an IC type of each of the one or more ICs based on the package image; selecting one or more reference images from a reference library that correlate to each of the IC types; imaging by X-ray the one or more ICs to provide at least one X-ray image of the one or more ICs; performing in any order: comparing an internal lead frame structure of the one or more ICs to the one or more reference images from the reference library to determine a first numerical indicator of the one or more ICs, by comparing by computer pattern matching the at least one X-ray image of the one or more ICs to a corresponding reference lead frame in the one or more reference images from the reference library; and determining a metallic composition of the internal lead frame of the one or more ICs based on the at least one X-ray image of the one or more ICs or another X-ray image of the one or more ICs, and comparing the metallic composition of the internal lead frame of the one or more ICs to a corresponding reference lead frame composition recalled from the reference library based on each of the IC types to determine a second numerical indicator; calculating an indication of authenticity based on the first numerical indicator and the second numerical indicator; and accepting or rejecting the one or more ICs based on the indication of authenticity.

In one embodiment, the step of pattern matching the package image of the one or more ICs to identify includes pattern matching a package mark selected from the group consisting of a manufacture logo, a manufacturer mark, a date code, a number, and an alpha numeric marking to one or more respective marks on the package image of the one or more ICs to identify by computer an IC type of each of the one or more ICs based on the package image.

In another embodiment, the step of pattern matching the package image of the one or more ICs further includes pattern recognition of the package mark.

In yet another embodiment, the step of pattern recognition of the package mark further includes optical character recognition of the mark followed by a comparison of one or more alphanumeric characters.

In yet another embodiment, the method further includes as part of the step of determining in any order, determining a third numerical indicator based on pattern matching the package image to the one or more reference images from the reference library that correlate to each of the IC types, and wherein the step of calculating the indication of authenticity includes calculating the indication of authenticity based on the first numerical indicator and the second numerical indicator and the third numerical indicator.

In yet another embodiment, the step of determining the third numerical indicator is based on pattern matching the package image to the one or more reference images from the reference library includes pattern recognition of a package mark selected from the group consisting of a manufacture logo, a manufacturer mark, a date code, a number, and an alpha numeric marking.

In yet another embodiment, the step of pattern recognition of the package mark further includes optical character recognition of the mark followed by a comparison of one or more alphanumeric characters.

In yet another embodiment, the step of comparing the internal lead frame structure includes comparing a parameter selected from the group consisting of a geometry, a shape, a size, an area, and a dimension between features.

In yet another embodiment, the step of comparing the internal lead frame structure further includes comparing on or more wire bonds to corresponding wire bonds in the one or more reference images from the reference library.

In yet another embodiment, the step of determining the metallic composition of the internal lead frame structure further includes determining a wire bond metallic composition of one or more wire bonds and comparing the wire bond metallic composition of one or more wire bonds to a corresponding composition of respective wire bonds in from the reference library.

In yet another embodiment, the step of imaging by X-ray the one or more ICs is performed with an X-ray dose that prevents damage to the one or more ICs by ionizing radiation.

In yet another embodiment, the method further includes the step of displaying on a computer display one or more of the at least one X-ray image of the one or more ICs showing differences between the one or more of the at least one X-ray image and the one or more reference images from the reference library.

In yet another embodiment, the step of imaging by X-ray the one or more ICs includes imaging by a transmissive X-ray technique.

In yet another embodiment, the step of imaging by X-ray the one or more ICs includes imaging by an X-ray technique selected from the group consisting of computed tomography (CT) 2.5D & 3D, tomosynthesis, crystalline Backscatter, X-ray laminography, EDX—Energy Dispersive X-ray spectroscopy, XRF—X-Ray fluorescence, and radiographic imaging 2D.

In yet another embodiment, the step of imaging optically includes imaging optically in a human visible wavelength spectra the package of one or more ICs to provide the package image of the one or more ICs.

In yet another embodiment, the step of imaging optically includes imaging optically in an infrared (IR) wavelength spectra or a ultraviolet (UV) wavelength spectra the package of one or more ICs to provide the package image of the one or more ICs.

According to another aspect, a system for counterfeit IC detection includes a computer programmed to perform the counterfeit IC detection and configured to run software to perform the counterfeit IC detection, the software provided on a non-volatile memory. A reference library is communicatively coupled to the computer. The reference library includes a plurality of reference images that correlate to IC types and composition data for materials of the IC types. An optical imager is communicatively coupled to the computer to provide a package image of the one or more ICs to identify one or more IC types and to select the one or more reference images from the reference library that correlate to each of the one or more IC types. An X-ray imager is communicatively coupled to the computer to provide at least one X-ray image of the one or more ICs and to compare by computer pattern matching the at least one X-ray image of the one or more ICs to the one or more reference images from the reference library. A process running on the computer determines in any order, a first numerical indicator based on a pattern match of a spatial feature of the at least one X-ray image of the one or more ICs to the one or more reference images from an X-ray imager reference library, and a second numerical indicator based on a comparison of a metallic composition of a lead frame derived from the at least one X-ray image of the one or more ICs or another X-ray image of the one or more ICs and a respective composition for the IC type from the reference library, and determines an indication of authenticity based on the first numerical indicator and the second numerical indicator to provide an authenticity indication of the one or more ICs.

In one embodiment, the optical imager is selected from the group consisting of a camera, a video camera, a visible light imager, an infrared (IR) imager, and an ultraviolet (UV) imager.

In another embodiment, the system for counterfeit IC detection further includes another X-ray imager, and the composition is determined from another X-ray image which is made by the another X-ray imager.

In yet another embodiment, the X-ray imager is selected from the group consisting of a computed tomography (CT) 2.5D & 3D imager, a tomosynthesis imager, a crystalline backscatter imager, an X-ray laminography imager, an EDX—Energy Dispersive X-ray Spectroscopy imager, an XRF—X-Ray fluorescence imager, a radiographic imaging 2D imager and a transmissive imager.

In yet another embodiment, the reference library includes a data base stored on the non-volatile memory or another non-volatile memory at a location other than the computer.

The foregoing and other aspects, features, and advantages of the application will become more apparent from the following description and from the claims.

BRIEF DESCRIPTION OF THE DRAWINGS

The features of the application can be better understood with reference to the drawings described below, and the claims. The drawings are not necessarily to scale, emphasis instead generally being placed upon illustrating the principles described herein. In the drawings, like numerals are used to indicate like parts throughout the various views.

FIG. 6C shows a block diagram of an X-ray apparatus with a computer; and

DETAILED DESCRIPTION

Definitions

Figure 1:
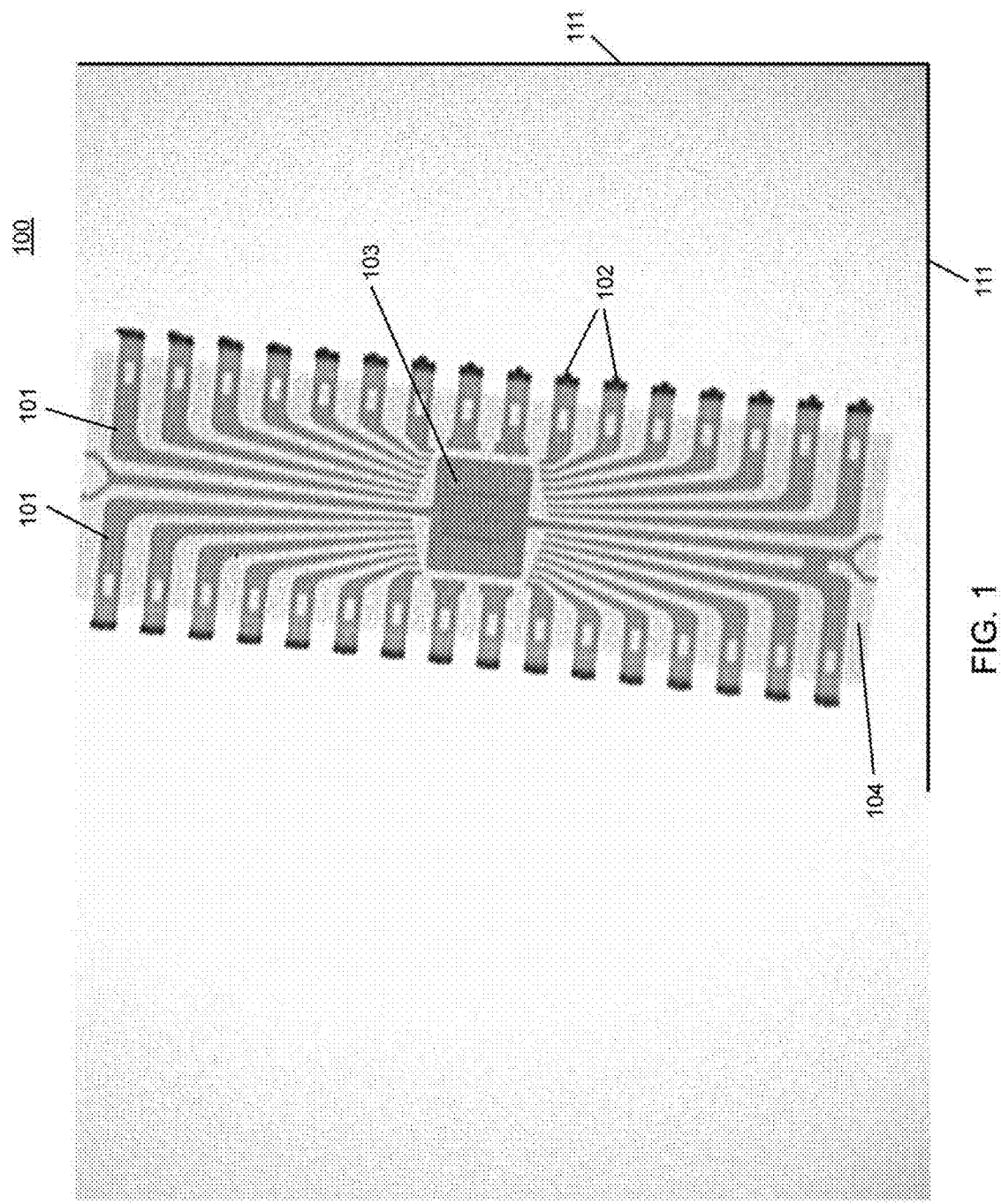
FIG. 1 shows an exemplary X-ray image of a 32 pin IC.

"Integrated Circuit" (IC) is defined as including all types of integrated electronics parts. Such parts include monolithic ICs (typically having a single die or die substrates within an IC package) as well as IC hybrids which might include one or more internally interconnected die or die substrates.

"Visible light" is defined herein as any non-ionizing light radiation. For example, visible light as used herein includes infrared (IR) light, the "human visible" light spectra, and ultra-violet (UV) light. Visible light as used herein does not include, for example radiation in the X-ray or gamma ray wavelengths.

"X-ray" radiation includes any X-ray wavelength as known by convention to those skilled in the art of X-ray technology. X-ray radiation is typically understood to be an ionizing radiation.

As described hereinabove, counterfeit detection, particularly in older or obsolete IC types, is problematic. Most of such older, often now obsolete IC types do not have the modern anti-counterfeiting measures built in to them. Many critical electronics designs using older and obsolete IC types are still in use today. Some of these designs are still being used to produce new equipment because of a proven record of high performance and/or high reliability. In other cases, older IC types are needed for repair and/or replacement inventory. Some of the older equipment that uses older IC types is used in safety of life applications. In many such applications, failure of equipment malfunction caused by a counterfeit IC can lead to loss of life and other catastrophic consequences (e.g. an aircraft incident or crash, or failure to deliver munitions to an intended target). There is a continuing need for new and reliable anti-counterfeiting systems and methods, particularly with respect to older IC types.

In co-pending U.S. patent application Ser. No. 14/194,127, filed Feb. 28, 2014, SYSTEM AND METHOD TO AUTHENTICATE INTEGRATED CIRCUITS, applicants described a visible light system and method to authenticate ICs using reference package images and reference die images by use of cameras, high resolution cameras, and microscopes and visible light. The '127 application is incorporated herein by reference in its entirety for all purposes.

As effective as the system and method of the '127 application is, there is still a need for additional IC authentication systems and methods.

One reason for additional anti-counterfeiting techniques is to thwart attempted circumvention of any particular counterfeiting detection strategy. Another reason is the continued search for systems and methods either working alone or in combination with other anti-counterfeiting techniques which can improve throughput, efficiency, and accuracy of IC authentication systems and methods. Reducing the cost of IC authentication is also a continuing goal. Also, the system and method described hereinbelow can be used for non-destructive IC authentication.

IC Lead Frames

ICs include one more die or substrates having electronic components formed thereon. Typically there is a metal structure called a lead frame which forms the leads and where used, pins, and any other electro-mechanical structure which provides the electrical connections to the IC package and to the one or more die within. Inside the IC package, there is some means of making electrical connections from points on the IC die to an individual leads of the lead frame. Particularly in older IC types, such electrical connections were made by very small wires, each of the wires bonded at one end to a pad on the die and at the other end to a lead of the lead set. The points of connection of the small wires to a pad on the die or to the lead frame are typically called wire bonds.

There are many types of lead frames which have been used by various manufacturers over the years. Some lead frame designs are industry wide standards. Other lead frame designs are unique to certain IC manufacturers. Similar IC type numbers are typically manufactured in two or more package types, for example, in a plastic package, a ceramic package, and a metal package. The lead frame design and/or lead frame metallic material composition might be different between the two or more package types. However, it can generally be known from IC manufacturing records what lead frames were used to manufacture a particular type of IC. Alternatively, known specimens of authentic ICs can generally be disassembled or otherwise analyzed as described hereinbelow to reveal the composition and style of the authentic IC type's lead frame.

X-ray Imaging

It was realized that an X-ray image of an IC can be used for IC authentication or as part of an IC authentication system. An X-ray system and method for risk mitigation in regard to counterfeit component parts such as ICs can be advantageous because the authentication testing process can be a non-destructive process because the IC package does not need to be opened. For example, an X-ray image of an IC can show enough detail of the lead frame to compare the shape and size of the lead frame to the lead frame design that was originally used to manufacture any given IC type and variant of that type (e.g. different package types and/or "grades" of the IC type).

Where the original lead frame geometry and/or lead frame material composition data is not available from the original manufacturer data, reference X-ray images and/or reference lead frame material composition data (e.g. text data and/or reference X-ray derived material composition data) can be created from one or more sample parts which are known to be authentic ICs. The authenticity of the sample parts can also be determined by traceable records and/or visible light optical methods such as are described in the '127 application discussed hereinabove.

Reference X-ray images can thus be created from original manufacturer data, actual images of known authentic ICs, or by any other suitable means. Reference images can be assembled and/or combined into one or more reference libraries. There can be X-ray image libraries and/or such reference X-ray images can be combined into more general image libraries which include other types of images, such as, for example, optical (visible light) reference die images, optical images of actual lead frames and/or reference package images. Such images can be indexed by IC type or any suitable IC identification number. There can be different reference X-ray images for variants of an IC type number, different production runs, changes in production methods, lead frame sizes and/or shapes, lead frame materials, etc. Also, there can be different reference images where an IC type was second sourced by one or more other IC manufacturers, or a company was purchased later by another IC company which made changes to the lead frame or other aspects of that IC type's production line.

It was also realized that in addition to studying the lead frame of an IC type under study for authentication, other indicia of authenticity can be developed from an X-Ray image. For example, the X-ray image of an IC can be evaluated for authenticity of one or more of the wire bonds. Other features of the X-ray of an IC being evaluated can also be compared to a reference X-ray image for that IC type.

Lead frames are particularly well defined and visible in an X-ray image of an IC. Each manufacturer used certain lead frame designs (e.g. lead frame style, shape, size) and certain lead frame materials (e.g. copper, kovar, etc.). There are also industry standard lead frame sizes and shapes. If an X-ray of an IC shows a lead frame shape that does not match the known lead frame shapes that were used for any particular type of IC (e.g. by computer image pattern matching), then the IC is known with a high level confidence to be different from those ICs made by the known IC manufacturer's for that IC type. If a different lead frame than expected is observed by the X-ray techniques described herein, it can be presumed that the IC is not authentic and therefore a counterfeit IC.

In most embodiments, an X-ray image of one or more ICs under test for authenticity is compared, such as by computer pattern matching, to at least one reference X-ray image for that IC type from a reference image library. The computer comparison of such digital images can include computer comparisons of geometry, shape, size, area, and dimensions between features in the image, or images, of the one or more ICs under test for authenticity, to at least one reference X-ray image selected from the reference library. It is understood that all such computer comparisons, especially comparisons of sizes and dimensions can be made with some tolerance value for acceptance or rejection. Most such comparisons might not result in a clear "Go/No Go" result (i.e. the results of a computer comparison can be more gray than "black and white"). Therefore, there can also be a computer generated confidence factor resulting from each comparison which can suggest a probability of authenticity, for example, over a range of 0% to 100%.

One or more reference X-ray images can be selected from the reference library by any suitable means or by any combination of suitable means. For example, one or more reference X-ray images can be selected from the reference library by use of an index system or index numbers (e.g. an index or record system of a reference library database), such as for example indexes of IC part numbers which include known variants of those part numbers. Also, reference X-ray images can be selected from the reference library by image recognition and/or by pattern matching one or more X-ray images of one or more ICs under test for authentication to one or more images in the reference library.

Another process to select one or more reference X-ray images from the reference library can be based on a combination of optical visible light methods and the X-ray authentication process. For example, in the methods described in the co-pending '127 application, there can be images (pictures) taken of an un-opened IC package. Using techniques such as computer optical character recognition (OCR) and/or computer image recognition and/or computer pattern matching, IC type information (at least what the type the IC under test "claims" to be) can be determined From such optical images, such as, for example, visible light images, e.g. camera (still or video) and/or microscope, or any other suitable visible light, infrared radiation (IR), or ultraviolet (UV) imager, ascertained IC type information can then be used to select one or more reference X-ray images from the reference library.

While typically camera images (digital photographs) via camera lens and/or microscope optics, such as were described in the co-pending '127 application, make use of the human visible light spectrum, any other wavelength of non-ionizing radiation can be used to generate such images. For example, there can be advantages in some counterfeit detection efforts to use infrared (IR) light illumination (which is typically outside of the human visible spectra), or ultra violet (UV) light, which also typically falls outside of the human visible light spectra, or light from the human visible spectra, or any combination thereof.

In some embodiments, X-ray apparatus in conjunction with computer analysis can also determine the metallic composition of the lead frame. Exemplary metals used in typical lead frames include kovar, copper and copper alloys, ferrous alloys containing nickel, cobalt, or chromium, nickel and nickel alloys, or other metallic materials, etc. Lead frame compositions typically follow industry specifications, such as, for example, American Society for Testing and Materials (ASTM) ASTM F375-89(2010), Standard Specification for Integrated Circuit Lead Frame Material. As with shape, size, and dimensions, material information can be stored in a reference library. It is unimportant to the process exactly how the reference lead frame material is stored, indexed, or cataloged, such as in a reference library computer database. For example each reference lead frame X-ray image can also include metal type material information. Or, a list of known materials used for a particular IC type can be indexed by the IC type or subsets of the IC type (e.g. by grade and/or package type, etc.). If a different lead frame material composition than expected is observed by the X-ray techniques described herein, it can be presumed that the IC is not authentic and therefore a counterfeit IC.

EXAMPLE 1

FIG. 1 shows an exemplary X-ray image of a 32 pin IC 100. The lead frame includes metallic conductors 101, pins 102, and metallic plate 103 which are contained within the package 104 of IC 100. It is unimportant that the image is skewed in the page frame. Techniques for automatically rotating an image to a vertical or horizontal position by computer process are well known in the art. Such straightening or alignment techniques, for example, are used to automatically align a document having text prior to running an optical character recognition (OCR) process. Reference lines 111 can be used by a computer image process to help define the bounds of the X-ray image and/or to facilitate dimensional measurements and/or other image processing routines.

EXAMPLE 2

Figure 2:
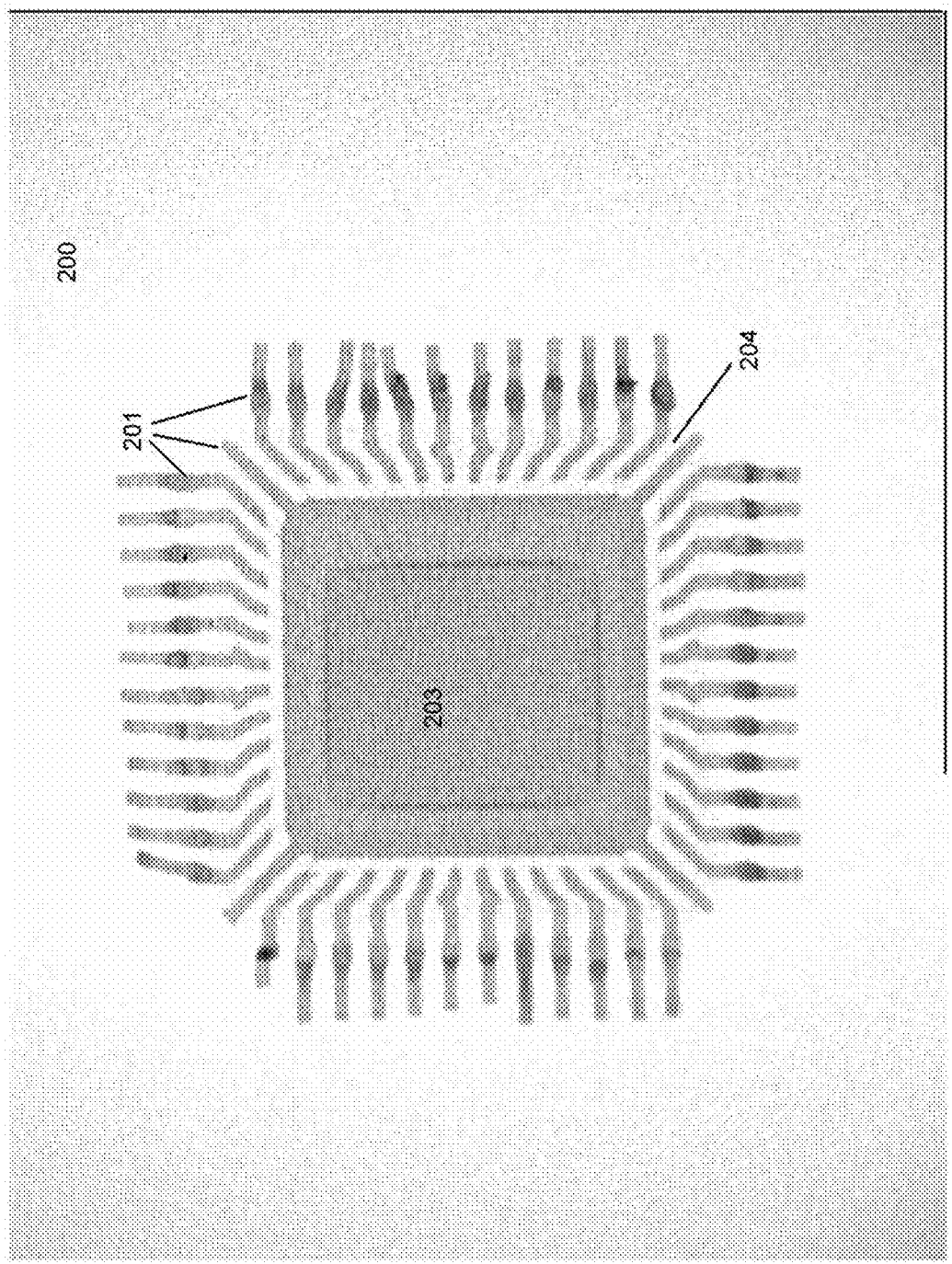
FIG. 2 shows an exemplary X-ray image of a 48 lead IC.

FIG. 2 shows an exemplary X-ray image of a 48 lead IC 200. The lead frame includes metallic conductors 201 and metallic plate 203 which are contained within the package 204 of IC 200.

EXAMPLE 3

Figure 3:
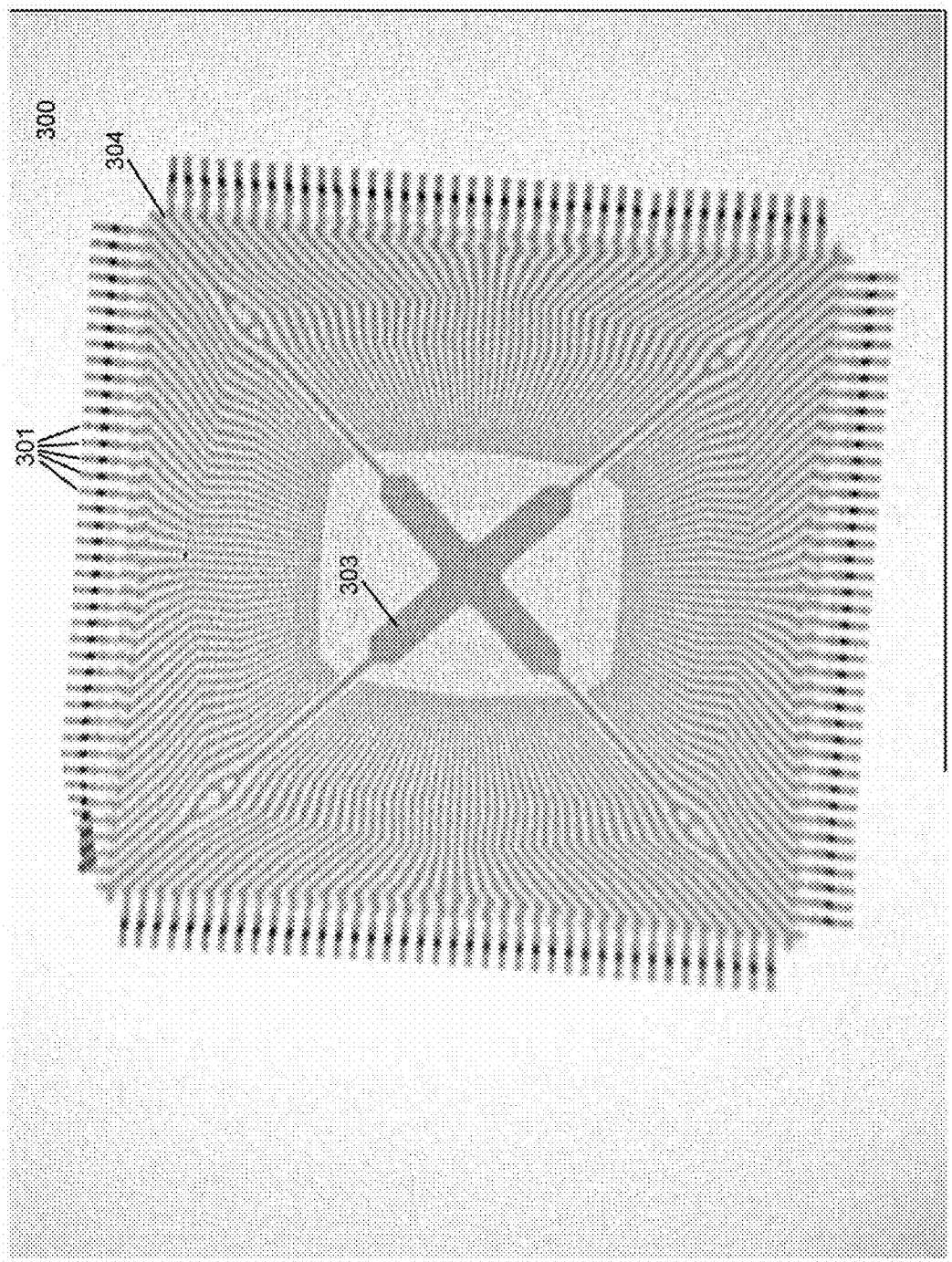
FIG. 3 shows an exemplary X-ray image of a 160 lead IC.

FIG. 3 shows an exemplary X-ray image of a 160 lead IC 300. The lead frame includes metallic conductors 301 and metallic plate 303 which are contained within the package 304 of IC 300.

EXAMPLE 4

Figure 4:
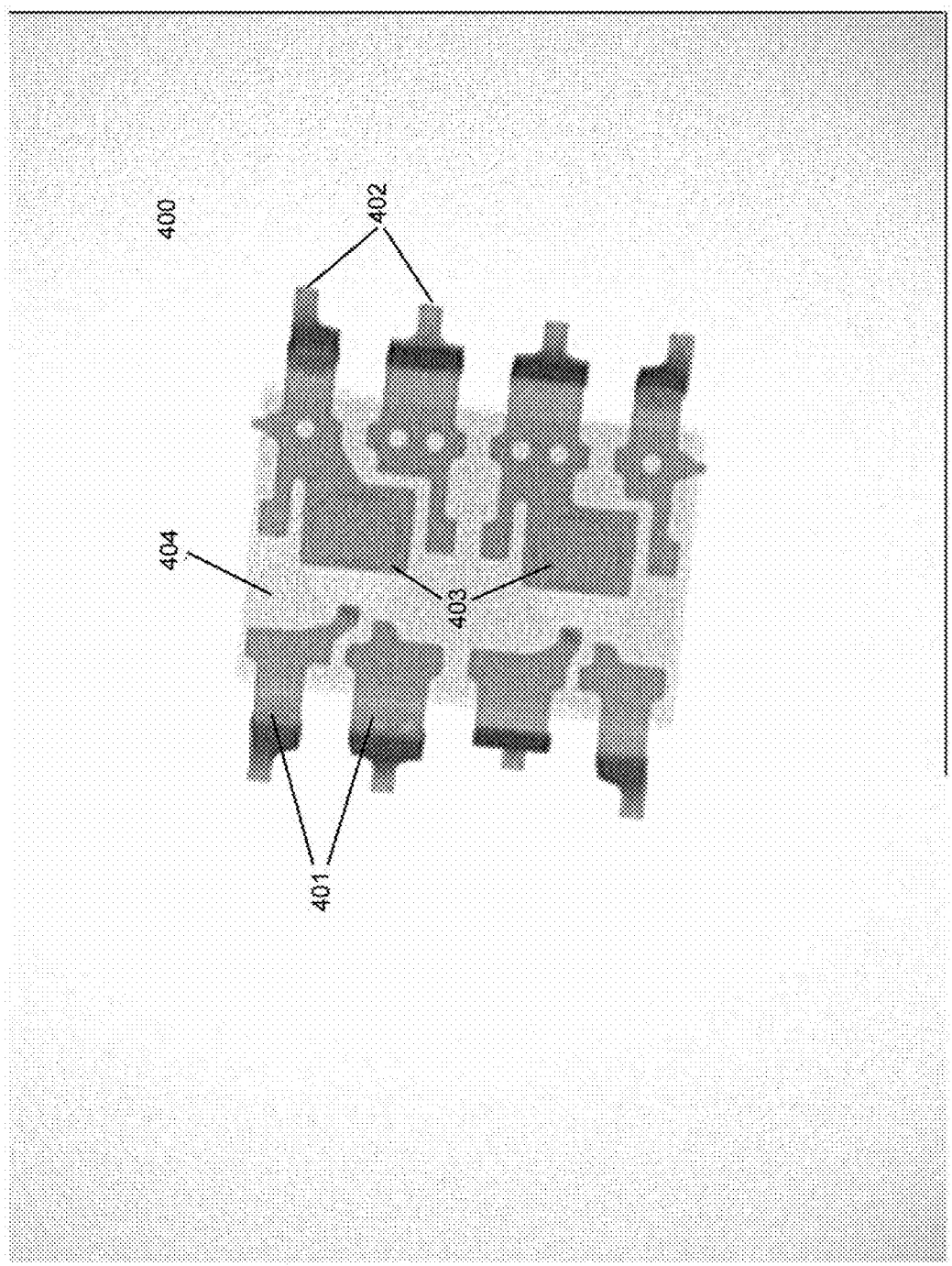
FIG. 4 shows an exemplary X-ray image of an 8 lead IC.

FIG. 4 shows an exemplary X-ray image of an 8 lead IC 400. The lead frame includes metallic conductors 401 and metallic plates 403 which are contained within the package 404 of IC 400.

EXAMPLE 5

Figure 5:
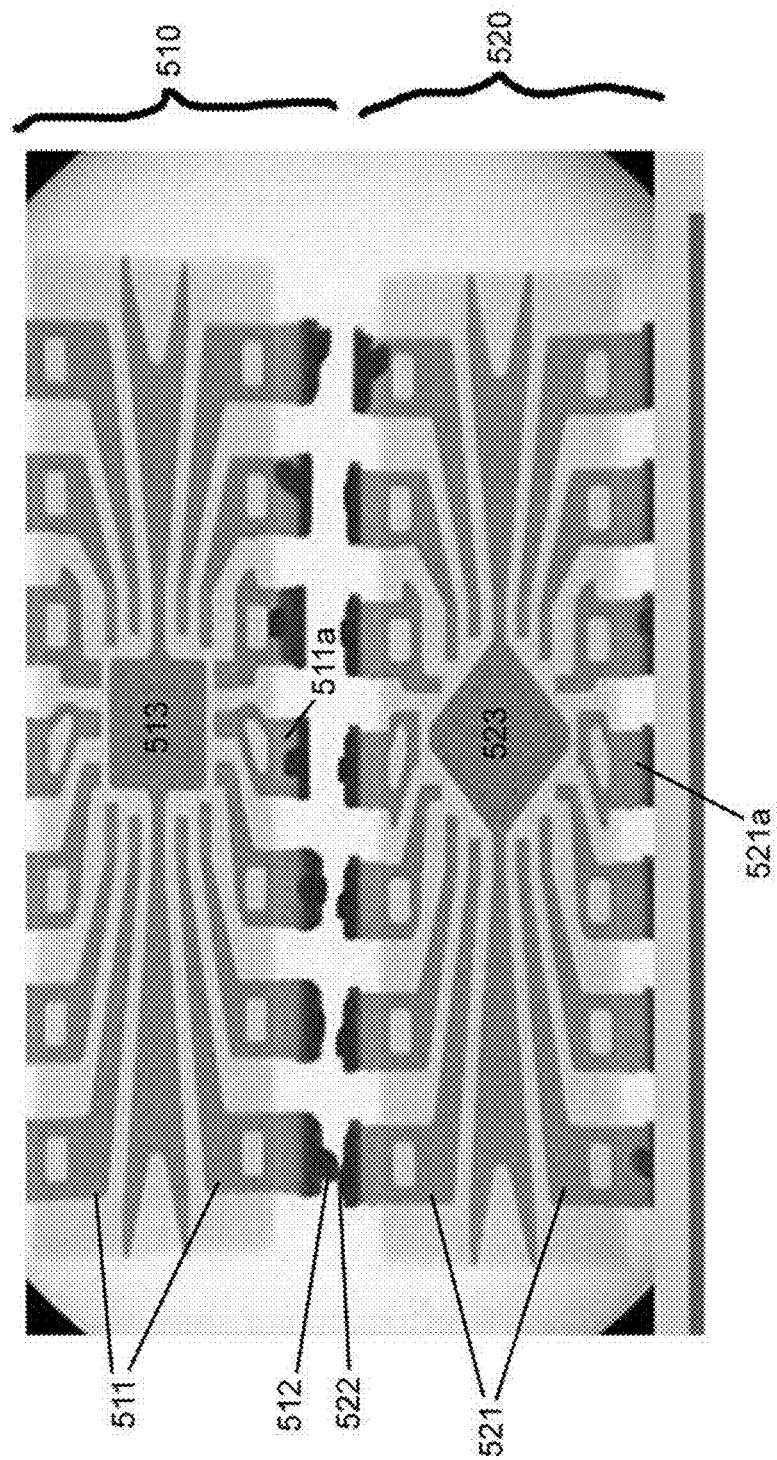
FIG. 5 shows an exemplary X-ray image of two hypothetically same type 14 pin ICs.

FIG. 5 shows an exemplary X-ray image of two hypothetically same 14 pin type ICs. The lead frame of IC 510 can be seen to include metallic conductors 511, pins 512, and metallic plate 513. The lead frame of IC 520 can be seen to include metallic conductors 521, pins 522, and metallic plate 523. In this hypothetical example, IC 520 is reference IC. A computer process to compare the X-ray image of IC 510 to the X-ray image of IC 520, such as by computer pattern matching and/or computer pattern recognition can show several differences. For example, the computer process can detect that the metallic plate 513 of IC 510 has a different shape than the metallic plate 523 of the reference IC, IC 520. Also, the computer process can detect that metallic conductor 511a of IC 510 has a different shape than metallic conductor 521a of the reference IC, IC 520. A computer process as described herein can identify either or both of such differences and determine the IC 510 to be non-authentic and presumed to be counterfeit.

Example 5 is a simplified example to show one exemplary comparison of X-ray images. More typically, a single X-ray image of an IC being checked for authenticity can be compared by computer process to one or more reference X-ray images in a reference library. Or, an X-ray image of a plurality of ICs under test for authenticity can be parsed by computer to compare by computer process one or more of the ICs of the single X-ray image to one or more reference X-ray images in a reference library. Also, while the differences of example 5 can also be detected by viewing, in many cases, the differences can be too small or subtle for human detection and can only be reliably detected by computer processing of the digital or digitized X-ray images.

In such cases a the hypothetical example 5 where a match is partial, but not complete, there can be further automatic comparisons by computer process to other images of authentic variants for the same IC type or IC part number. Where a match is found to another reference X-ray image of a known variant of the same IC part number, the IC might be found by the same computer process to be authentic. A common form of counterfeiting is to re-label an IC to a higher grade or similar part number with higher economic value. Therefore where a "good" computer match is found to another variant of the same type IC, it is often just another form of counterfeit IC, and a falsely labeled IC is not authentic despite the match to a genuine manufactured part (albeit of a different, typically lower cost grade).

Another similar example of such counterfeiting techniques is to re-label a commercial grade part to a military grade part. In such cases, there might still be a match between an X-ray image of an IC undergoing a computer authentication process and a reference X-ray image from the reference library, yet the IC is still very clearly a counterfeit IC because of the new false labeling. In some embodiments, a computer authentication process as described herein can report the match and the IC type of the actual IC found during the authentication process.

Another common form of counterfeiting is where some formerly legitimate IC die stock has been acquired by a counterfeit IC manufacturer. The counterfeit IC manufacturer assembles to former legitimate die into a "new" IC package using a lead frame which was never used by any of the original manufacturers of that IC type or IC number. The computer authentication process as described herein identifies an IC under the computer authentication process described herein to be non-authentic because the "found" lead frame in the X-ray image of the part undergoing the computer authentication process does not match any of the lead frames that were present in the X-ray image library for that IC type or IC part number. However, the computer process does identify a known lead frame type. In some embodiments, the computer process can report the IC as not authentic and also report the known lead frame type found in the X-ray image. As described hereinabove, even if the geometry (e.g. size, shape, and dimensions) of the lead frame matches a known industry lead frame type, there can still be a rejection of authenticity based an X-ray process derived metallic composition of the lead frame (i.e. a known type lead frame was used, but not the expected lead frame type for that IC type). That is, in some embodiments, even where the geometry is a substantial match, an IC under authentication testing can still be found to be non-authentic based on the measured by X-ray lead frame metallic composition.

Computer process system example: In one embodiment, any suitable X-ray apparatus which includes a means to generate an X-ray digital image is provided. The X-ray apparatus is configured to accept one or more ICs to be imaged by X-ray radiation. A computer is provided which is communicatively coupled to the X-ray apparatus. The computer can receive (e.g. by wired or wireless communication with the X-ray apparatus) one or more X-ray images of the one or more ICs under test.

Figure 6A:
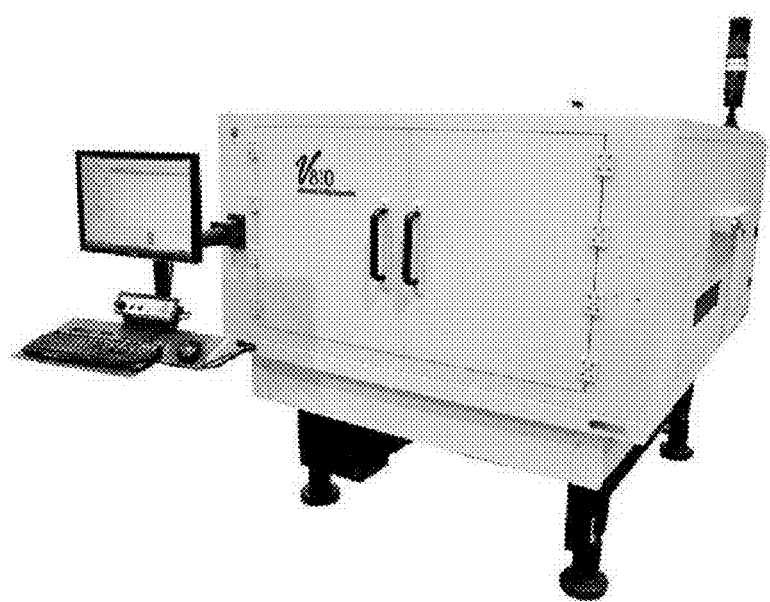
FIG. 6A shows an illustration of an exemplary Vitrox V810 X-ray apparatus believed suitable to perform the inventive method.
Figure 6B:
FIG. 6B shows an illustration of an exemplary Agilent X-ray inspection apparatus also believed suitable to perform the inventive method.

FIG. 6A shows an illustration of an exemplary VITROX V810 X-ray apparatus believed suitable to perform the inventive method. FIG. 6B shows an illustration of an exemplary Agilent X-ray inspection apparatus also believed suitable to perform the inventive method. FIG. 6C shows a block diagram of a system suitable for performing the IC authentication process described herein. An X-ray apparatus 101 is communicatively coupled via any suitable communication method 105 (e.g. GPIB, HPIB, USB, RS-232, etc.) with a computer 102 having a computer readable non-transitory storage medium (not shown in FIG. 6C) which includes a computer readable code configured to run the IC authentication process on computer 102. A computer 102 typically also includes at least one computer display 103 and a keyboard 104. Other user interface devices, such as for example a computer mouse or trackball can be communicatively coupled to computer 102.

X-ray apparatus and human safety: In one embodiment, one or more X-ray images of one or more ICs under test for authenticity are taken and transferred to the computer. The control of the X-ray apparatus and initiation of X-ray images can be controlled by the computer process. It is understood that human safety controls and interlocks will typically be present so that any human activity (e.g. where IC's are manually placed on an X-ray platform or table surface) or where there is proximate human presence to the X-ray apparatus, the X-ray apparatus can be made to inhibit X-ray emission to prevent unnecessary human exposure by X-rays and provide safety of life measures with regard human presence. In some embodiments, there can be computer controlled electromechanical apparatus to load parts to be tested onto the X-ray apparatus platform or X-ray table and to remove them after the X-ray images have been taken. Such automatic loading and removal of components under test can minimize human presence. In other embodiments, the X-ray emission will be of sufficiently low energy and/or sufficient low intensity that a human operator can remain in the general vicinity of the X-ray apparatus without receiving any significant radiation dose. Any suitable shielding (e.g. lead shielding) can also be used to further enhance human radiation safety measures.

Computer process example: Now, continuing with the exemplary computer process, the one or more images of the ICs under test for authenticity can be used to locate by computer process (e.g. pattern matching) one or more suitable reference X-ray images from the reference library. The computer process can then compare the one or more images of the ICs under test for authenticity to the one or more reference X-ray images from the reference library using any of the techniques described herein including, for example, geometry, size, dimensions, and/or shape. The computer comparison can be particularly centered about the portion of the X-ray images related to the IC lead frame. There can also be computer comparisons between the images of the ICs under test for authenticity to the one or more reference X-ray images from the reference library based on other indicia, such as for example package dimensions. There can also be computer comparisons between the one or more images of the ICs under test for authenticity to the one or more reference X-ray images from the reference library or to text based information related to those IC types and IC type variants based on lead frame material composition.

Once the X-ray images have been selected from the reference library, it is unimportant to the process in what order the computer comparisons for the determination of authenticity are made. For example, the first determination can be based on a comparison of lead frame metallic composition, followed by a determination based on lead frame geometry, size, dimensions, and/or shape. Or, the process can first make a comparison between the one or more images of the ICs under test for authenticity to the one or more reference X-ray images from the reference library based on lead frame geometry, size, dimensions, and/or shape, followed by a determination based on a comparison of lead frame metallic composition. Or, in other embodiments, there can be a determination of IC authenticity based only on a comparison of lead frame metallic composition, without any further testing. Or, in other embodiments, there can be a determination of IC authenticity based only on a comparison of lead frame geometry, size, dimensions, and/or shape, without any further testing.

Process example: While in some embodiments non-destructive X-ray testing for authenticity as described herein is advantageous, in other embodiments, X-ray testing can be yet another process step as part of a destructive IC authentication process (e.g. an authentication process where the die of an IC are exposed to view by opening the IC package). For example, in some embodiments, X-ray testing for authenticity as described herein can be performed before, during, or after, any of the process steps (e.g. visible light imaging of an IC die) described in the co-pending '127 application.

Figure 7:
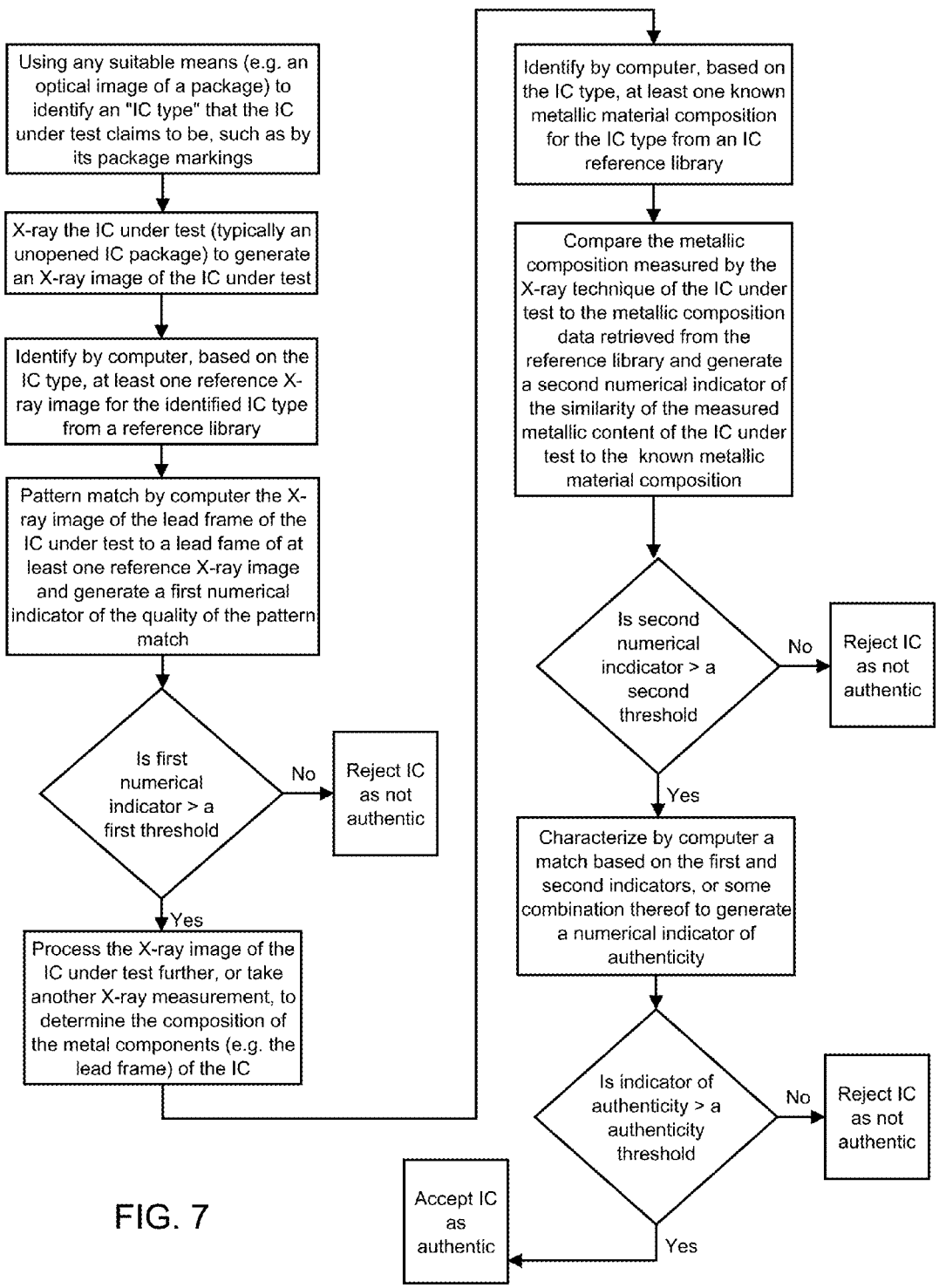
FIG. 7 shows an exemplary process block diagram.

Process flow chart: FIG. 7 shows an exemplary process block diagram. According to the exemplary process of FIG. 7, using any suitable means (e.g. an optical image of a package) an "IC type" that the IC under test claims to be, can be first determined, such as by its package markings. An X-ray is made of the IC under test (typically an unopened IC package) to generate an X-ray image of the IC under test. Based on the IC type which the IC under test claims to be (e.g. by the package marking), at least one reference X-ray image for the identified IC type is retrieved from a reference library. A pattern match is made by computer of the X-ray image of the lead frame of the IC under test to the lead frame of at least one reference X-ray image and a first numerical indicator of the quality of the pattern match is generated. If the first numerical indicator is less than or equal to a first threshold, the IC under test is determined not to be an authentic IC. If the first numerical indicator is greater than the first threshold, the X-ray image of the IC under test is further processed, or another X-ray measurement is made, to determine the composition of the metal components (e.g. the lead frame) of the IC under test. Based on the IC type claimed by the IC under test, at least one known metallic material composition for the IC type is retrieved by computer from an IC reference library. One or more of the metallic compositions measured by the X-ray technique of the IC under test are compared to the metallic composition data retrieved from the reference library and a second numerical indicator of the similarity of the measured metallic content of the IC under test to the known metallic material composition is generated. If the second numerical indicator is less than or equal to a second threshold, the IC under test is determined not to be an authentic IC. If the second numerical indicator is greater than the first threshold, a match based on the first and second indicators, or some combination thereof is characterized to generate a numerical indicator of authenticity. If the indicator of authenticity is less than or equal to an authenticity threshold, the IC under test is determined not to be an authentic IC. If the indicator of authenticity is greater than the authenticity, the IC under test can be accepted as authentic.

EXAMPLE 6

Applying the process of FIG. 7 to the hypothetical example of FIG. 5, it is contemplated that a first pattern matching of the X-ray image of the lead frame of IC 510 to the reference X-ray image of the lead frame of IC 520 would yield a first numerical indicator of 90%, however were the first threshold set to 95%, IC 510 would be rejected as not authentic. Here, the process does not need to progress to comparing the composition of the two lead frames. Where that comparison is made as a first or later process step, the compositions should typically be substantially identical.

It is unimportant to the process whether the test order is reversed in time order. For example, the IC under test can be first evaluated for metallic composition using X-ray techniques and a computer comparison of material types, followed by a comparison by computer of an X-ray image of the IC under test to a reference X-ray image retrieved from an image library.

X-ray Dose

X-rays are an ionization radiation. Various X-ray parameters which can be considered during IC testing include X-ray energy, X-ray intensity, and duration of exposure. X-ray energy and intensity are typically established by the X-ray hardware, such as the X-ray tube used in the X-ray apparatus, and the high voltage and X-ray tube electrical current settings. Once other X-ray parameters are set, dosage is mostly a function of the time duration of the X-ray pulse, pulses, or one or more X-ray pulses in a crystalline backscatter apparatus, or successive X-ray scans in a computed tomography (CT) X-ray apparatus.

ICs can be damaged by too high an X-ray dosage. Many studies have been made, particularly by national organizations such as NASA, and the Department of Energy National Laboratories on what levels of ionizing radiation various types of ICs and ICs technologies can be exposed to without suffering radiation related damage. Methods to test semiconductor devices of the effects of ionizing radiation are well known. Methods for testing are outlined by standards organizations such as the American Society for Testing and Materials (ASTM). One such exemplary method is described, for example, in ASTM F1892-12 Standard Guide for Ionizing Radiation (Total Dose) Effects Testing of Semiconductor Devices. Therefore, while evaluating the authenticity of one or more ICs under test using the processes described herein, X-ray dosage will need to be limited to a dosage less than known damaging dose for any given IC type and/or IC technology.

Exemplary X-ray Types

Types of X-ray techniques believed suitable to perform the IC X-ray authentication techniques described herein, include but are not limited to Transmissive X-ray, Computed Tomography (CT) 2.5D & 3D, Tomosynthesis, Crystalline Backscatter, X-ray Laminography, EDX—Energy Dispersive X-ray Spectroscopy, XRF—X-Ray Fluorescence, and Radiographic imaging 2D.

Exemplary X-ray Machines

Exemplary X-ray Machines suitable to perform the IC X-ray authentication techniques described herein, include the model TR7680 available from TRI of Taipei, Taiwan; the model V810, available from Vitrox of Malaysia; the X7056RL, available from Viscom of Hanover, Germany; the model Opticon X-line 3D, available from Goepel of Jena, Germany; the model VT-X700, available from OMRON of Japan; the model X3+ available from MatriX Technologies of Feldkirchen, Germany; the model X3 available from Yestech of Carlsbad, Calif.; the model 5300, manufactured by Agilent Technologies, Singapore; models available from the TRION corporation, the model XT V 160 available from Nikon of Japan; models available from Teradyne of North Reading, Mass., from YXLON of Hamburg, Germany; from GE Sense & Inspection of Phoenix, Ariz., X-technology (fein focus) of San Antonio, TX, and NSI (North Star Imaging), e.g. the model Express-CT of Rogers, Minnesota. A Vitrox 810 X-ray inspection machine to be used for further testing of the techniques described herein includes, for example, a 3D CT capability believed useful for creating both X-ray images of an IC under test as well as reference X-ray images by X-ray imaging known authentic IC types.

Exemplary Pattern Matching

Image analysis, including pattern recognition and pattern matching as described hereinabove, can be accomplished using commercial image processing routines available in high level scientific and engineering computer programs or libraries, such as, for example, LabView available from National Instruments of Austin, TX, Keyence (Itasca, IL), REVImg, TinMan, and OpenCV (opencv.org). Alternatively such routines can be performed by custom written software or software modules based on pattern recognition and pattern matching techniques as are known in the art.

The authentication techniques described hereinabove are believed to be applicable to any type of IC manufactured by any known process technology. It is unimportant to the process what fabrication process, such as for example, fabrication techniques including XFET, Bipolar, CMOS, etc. was used to make the IC. Similarly, it is unimportant to the process what type of materials and semiconductor materials were used to make the IC, such as for example, $SiO_2$, GaAs, etc.

It will be understood by those skilled in the art that images and related materials in the reference library can be indexed and cataloged, especially, for example, to link reference images and reference materials to particular ICs and to reference X-ray images of particular ICs. It is unimportant to the process what data structure, linking method, and/or database type might be used to organize and search the reference library. Any suitable data structure, database, and linking techniques can be used to organize and/or search a reference library as described herein.

It will also be understood by those skilled in the art that actual X-ray images and/or images of packages of ICs under evaluation and/or images in the reference library can be edited, sized, or otherwise enhanced to facilitate efficient image comparisons such as pattern recognition and pattern matching as described hereinabove. Exemplary suitable operations include stitching two or more images together, frame averaging, and zooming It will also be understood that in some embodiments there can be added any suitable security measures by hardware and/or software to protect, for example the reference library from falling into the possession of an IC counterfeiter.

Any firmware and/or software to perform the method for counterfeit IC detection described hereinabove can be provided on a computer readable non-transitory storage medium. Images and other indexed data (e.g. composition data) of the reference library in any suitable form (e.g. as an indexed database) can also reside on a computer readable non-transitory storage medium. The reference library can reside on a memory of the computer which runs the counterfeit IC detection process, or the reference library while accessible by the computer which runs the counterfeit IC detection process, can reside at another location and be communicatively coupled to the computer by any suitable network, such as, for example a local network or the Internet. A computer readable non-transitory storage medium as non-transitory data storage includes any data stored on any suitable media in a non-fleeting manner. Such data storage includes any suitable computer readable non-transitory storage medium, including, but not limited to hard drives, non-volatile RAM, SSD devices, CDs, DVDs, etc.

It will be appreciated that variants of the above-disclosed and other features and functions, or alternatives thereof, may be combined into many other different systems or applications. Various presently unforeseen or unanticipated alternatives, modifications, variations, or improvements therein may be subsequently made by those skilled in the art which are also intended to be encompassed by the following claims.

What is claimed is:

1. A method for counterfeit IC detection comprising:
   providing a computer, an optical imager communicatively coupled to said computer, an X-ray imager communicatively coupled to said computer, said computer programmed to perform said counterfeit IC detection;
   imaging optically a package of one or more ICs to provide a package image of said one or more ICs;
   pattern matching said package image of said one or more ICs to identify by computer an IC type of each of said one or more ICs based on said package image;
   selecting one or more reference images from a reference library that correlate to each of said IC types;
   imaging by X-ray said one or more ICs to provide at least one X-ray image of said one or more ICs;
   performing in any order;
   comparing an internal lead frame structure of said one or more ICs to said one or more reference images from said reference library to determine a first numerical indicator of said one or more ICs, by comparing by computer pattern matching said at least one X-ray image of said one or more ICs to a corresponding reference lead frame structure in said one or more reference images from said reference library; and
   determining a metallic composition of said internal lead frame structure of said one or more ICs based on said at least one X-ray image of said one or more ICs or another X-ray image of said one or more ICs, and comparing said metallic composition of said internal lead frame structure of said one or more ICs to a metallic composition of a corresponding reference lead frame structure recalled from said reference library based on each of said IC types to determine a second numerical indicator;
   calculating an indication of authenticity based on said first numerical indicator and said second numerical indicator; and
   accepting or rejecting said one or more ICs based on said indication of authenticity.

2. The method of claim 1, wherein said step of pattern matching said package image of said one or more ICs to identify comprises pattern matching a package mark selected from the group consisting of a manufacture logo, a manufacturer mark, a date code, a number, and an alpha numeric marking to one or more respective marks on said package image of said one or more ICs to identify by computer an IC type of each of said one or more ICs based on said package image.

3. The method of claim 2, wherein said step of pattern matching said package image of said one or more ICs further comprises pattern recognition of said package mark.

4. The method of claim 3, wherein said step of pattern recognition of said package mark further comprises optical character recognition of said mark followed by a comparison of one or more alphanumeric characters.

5. The method of claim 1, further comprising as part of said step of performing in any order, determining a third numerical indicator based on pattern matching said package image to said one or more reference images from said reference library that correlate to each of said IC types, and wherein said step of calculating said indication of authenticity comprises calculating said indication of authenticity based on said first numerical indicator and said second numerical indicator and said third numerical indicator.

6. The method of claim 5, wherein said step of determining said third numerical indicator based on pattern matching said package image to said one or more reference images from said reference library comprises pattern recognition of a package mark selected from the group consisting of a manufacture logo, a manufacturer mark, a date code, a number, and an alpha numeric marking.

7. The method of claim 6, wherein said step of pattern recognition of said package mark further comprises optical character recognition of said mark followed by a comparison of one or more alphanumeric characters.

8. The method of claim 1, wherein said step of comparing said internal lead frame structure comprises comparing a parameter selected from the group consisting of a geometry, a shape, a size, an area, and a dimension between features.

9. The method of claim 1, wherein said step of comparing said internal lead frame structure further comprises comparing one or more wire bonds to corresponding wire bonds in said one or more reference images from said reference library.

10. The method of claim 1, wherein said step of determining said metallic composition of said internal lead frame structure further comprises determining a wire bond metallic composition of one or more wire bonds and comparing said wire bond metallic composition of one or more wire bonds to a corresponding composition of respective wire bonds from said reference library.

11. The method of claim 1, wherein said step of imaging by X-ray said one or more ICs is performed with an X-ray dose that prevents damage to said one or more ICs by ionizing radiation.

12. The method of claim 1, further comprising the step of displaying on a computer display one or more of said at least one X-ray image of said one or more ICs showing differences between said one or more of said at least one X-ray image and said one or more reference images from said reference library.

13. The method of claim 1, wherein said step of imaging by X-ray said one or more ICs comprises imaging by a transmissive X-ray technique.

14. The method of claim 1, wherein said step of imaging by X-ray said one or more ICs comprises imaging by an X-ray technique selected from the group consisting of computed tomography (CT) 2.5D & 3D, tomosynthesis, crystalline Backscatter, X-ray laminography, EDX—Energy Dispersive X-ray spectroscopy, XRF—X-Ray fluorescence, and radiographic imaging 2D.

15. The method of claim 1, wherein said step of imaging optically comprises imaging optically in a human visible wavelength spectra said package of one or more ICs to provide said package image of said one or more ICs.

16. The method of claim 1, wherein said step of imaging optically comprises imaging optically in an infrared (IR) wavelength spectra or a ultraviolet (UV) wavelength spectra said package of one or more ICs to provide said package image of said one or more ICs.

17. A system for counterfeit IC detection comprising:
a computer programmed to perform said counterfeit IC detection and configured to run software to perform said counterfeit IC detection, said software provided on a non-volatile memory;
a reference library communicatively coupled to said computer, said reference library comprising a plurality of reference images that correlate to IC types and composition data for materials of said IC types;
an optical imager communicatively coupled to said computer to provide a package image of one or more ICs to identify one or more IC types and to select one or more reference images from said reference library that correlate to each of said one or more IC types;
an X-ray imager communicatively coupled to said computer to provide at least one X-ray image of said one or more ICs and to compare by computer pattern matching said at least one X-ray image of said one or more ICs to said one or more reference images from said reference library; and
said software running on said computer which determines in any order, a first numerical indicator based on a pattern match of a spatial feature of said at least one X-ray image of said one or more ICs to said one or more reference images from said reference library, and a second numerical indicator based on a comparison of a metallic composition of a lead frame derived from said at least one X-ray image of said one or more ICs or another X-ray image of said one or more ICs and a respective composition for the IC type from said reference library, and which determines an indication of authenticity based on said first numerical indicator and said second numerical indicator to provide an authenticity indication of said one or more ICs.

18. The system for counterfeit IC detection of claim 17, wherein said optical imager is selected from the group consisting of a camera, a video camera, a visible light imager, an infrared (IR) imager, and an ultraviolet (UV) imager.

19. The system for counterfeit IC detection of claim 17, further comprising another X-ray imager, and said composition is determined from another X-ray image made by said another X-ray imager.

20. The system for counterfeit IC detection of claim 17, wherein said X-ray imager is selected from the group consisting of a computed tomography (CT) 2.5D & 3D imager, a tomosynthesis imager, a crystalline backscatter imager, an X-ray laminography imager, an EDX—Energy Dispersive X-ray Spectroscopy imager, an XRF—X-Ray fluorescence imager, a radiographic imaging 2D imager and a transmissive imager.

21. The system for counterfeit IC detection of claim 17, wherein said reference library comprises a data base stored on said non-volatile memory or another non-volatile memory at a location other than said computer.

* * * * *